United States Patent [19]

Herrling et al.

[11] Patent Number: 4,916,125

[45] Date of Patent: Apr. 10, 1990

[54] METHOD OF TREATING MIGRAINE

[75] Inventors: Paul L. Herrling, Bern; Julian A. Gray, Binningen, both of Switzerland

[73] Assignee: Sandoz Ltd., Basel, Switzerland

[21] Appl. No.: 377,989

[22] Filed: Jul. 11, 1989

[51] Int. Cl.$^4$ .................. A61K 31/66; A61K 31/675
[52] U.S. Cl. .................................... 514/89; 514/114
[58] Field of Search ................................ 514/89, 114

[56] References Cited

PUBLICATIONS

Trends in Neuroscience, 10, pp. 8–13, (1987).
Brain Research, 457, pp. 226–240, (1988).
Neurology and Neurobiology, vol. 46, pp. 661–666, (1988).

*Primary Examiner*—Stanley J. Friedman
*Attorney, Agent, or Firm*—Gerald D. Sharkin; Robert S. Honor; Joseph J. Borovian

[57] ABSTRACT

A method of treating migraine in a subject in need of such treatment comprising administering to said subject a therapeutically effective amount of a phosphonic acid.

3 Claims, No Drawings

METHOD OF TREATING MIGRAINE

The present invention relates to a method of treating migraine in a subject in need of such treatment, which comprises administering to said subject a therapeutically effective amount of a compound of formula I

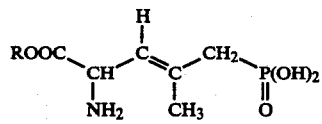    I wherein R is hydrogen or ethyl, or the compound of formula II

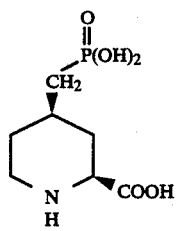    II or a pharmaceutically acceptable salt thereof.

The compounds of formula I are described in e.g. European Patent Application 233 154. The compounds of formula I contain one chiral centre at the carbon atom bearing the amino group and can therefore exist in racemic and optically-active forms. It is to be understood that the present invention encompasses the racemic and any optically active form. The substituents H and CH₃ at the double bond are in trans-configuration.

The compound of formula II is described e.g. in European Patent Application 203 891.

The compounds of formulae I and II can form acid addition and cationic salts. Acid addition salts include those formed with hydrochloric, hydrobromic, sulfuric, methanesulfonic, benzene-sulfonic, p-toluenesulfonic and trifluoroacetic acid. Cationic salts include ammonium, sodium, potassium, calcium, piperidinium, morpholinium or pyrrolidinium salts.

In accordance with the present invention it has now surprisingly been found that the compounds of formulae I and II exhibit spreading depression inhibiting activity in the frontal cortex of rats [method of R. Marrannes et al., Brain Res. 457 (1988) 226]. In this test the compounds increase spreading depression threshold and propagation time and reduce spreading depression duration at dosages of from 3 to 30 mg/kg i.p.

The compounds of formula I and II are, therefore, useful in the treatment of migraine, e.g. classical migraine.

For this indication the appropriate dosage will, of course, vary depending upon, for example, the compound employed, the host, the mode of administration and the nature and severity of the condition being treated. However, in general, satisfactory results in animals are indicated to be obtained at a daily dosage of from about 3 to about 30 mg/kg animal body weight. In larger mammals, for example humans, an indicated daily dosage is in the range from about 5 to about 800 mg of a compound of formula I or II conveniently administered, for example, in divided doses up to four times a day.

The compounds of formulae I and II may be administered as such or as their pharmaceutically acceptable salts. Such salts exhibit the same order of activity as the compounds of formula I or II.

The present invention further provides pharmaceutical compositions comprising a compound of formula I or II or a pharmaceutically acceptable salt thereof in association with a pharmaceutically acceptable carrier or diluent.

The compounds of formulae I and II may be administered by any conventional route, in particular enterally, preferably orally or parenterally. The compounds of formulae I and II may be administered as such or admixed with conventional pharmaceutical carriers. For example, for oral administration e.g. in the form of tablets or capsules, a compound of formula I or II may be admixed with conventional pharmaceutically acceptable excipients, e.g. inert diluents, such as lactose, mannitol, calcium sulfate, microcrystalline cellulose; disintegrating agents, e.g. starch, sodium carboxymethyl cellulose, sodium carboxymethyl starch, alginic acid, crospovidone; binding agents such as cellulose derivates (methyl-, hydroxymethyl-, hydroxypropylmethyl-,), povidone, gelatine; lubricating agents e.g. siliciumdioxide, stearic acid, magnesium or calcium stearate; hydrogenated oils such as castor oil, glycerolesters e.g. palmitostearate and/or flavouring, colouring and sweetening agents. The tablets my be uncoated or coated by known techniques to delay distintegration and absorption in the gastrointestinal tract and thereby provide a sustained action over a longer period. Parenteral compositions are preferably in the form of a sterile inject aqueous solution. Such aqueous solutions should be suitably buffered if necessary and rendered isotonic with sufficient saline. Optionally a preservative, such as benzyl alcohol, can be added.

A unit dosage may contain from about 1.25 to about 400 mg of a compound of formula I or II or a pharmaceutically acceptable salt thereof.

The pharmaceutical compositions can be prepared according to conventional techniques.

For the manufacture of tablets, a compound of formula I or II can be mixed with lactose and granulated with water, 0.5% sodium alginate or 5% hydroxypropylmethylcellulose solution. The dried granulate is compressed into tablets in the presence of about 20% of corn starch and 1% of magnesium stearate. In this way, there are obtained, e.g. tablets of the following composition:

| INGREDIENTS | TABLET WEIGHT (mg) |
|---|---|
| cis-4-phosphonomethyl-2-piperidine-carboxylic acid | 50 |
| Lactose | 97 |
| Corn Starch | 40 |
| Hydroxypropylmethylcellulose | 10 |
| Magnesium stearate | 2 |
| Siliciumdioxide | 1 |
| | 200 |

These tablets, which are provided with a crackline, can be administered orally in a dosage of e.g. one half to one tablet up to 4 times a day.

Capsules may contain the active agent alone or admixed with an inert solid excipient, for example as mentioned above.

Capsules containing the ingredients indicated below may be prepared by conventional techniques and are administered at a dose of e.g. one capsule up to 4 times a day.

| INGREDIENTS | CAPSULE WEIGHT (mg) |
| --- | --- |
| E-2-amino-4-methyl-5-phosphono-3-pentenoic acid ethyl ester | 50 |
| Inert solid excipient (corn starch, lactose, aerosil, magnesium stearate) | 250 |

Similarly tablets and capsules containing 25 mg and 100 mg of a compound of formula I or II may be prepared.

The following injectable solution is formulated with the indicated amount of active agent using conventional techniques. The injectable solution is suitable for administration e.g. once a day.

| INGREDIENTS | STERILE INJECTABLE SOLUTION WEIGHT (mg/ml) |
| --- | --- |
| cis-4-phosphonomethyl-2-piperidine-carboxylic acid | 25 |
| Sodium chloride | 7.0 |
| Potassium dihydrogen phosphate | 3.63 |
| Disodium hydrogen phosphate | 5.68 |

| INGREDIENTS | STERILE INJECTABLE SOLUTION WEIGHT (mg/ml) |
| --- | --- |
| Benzyl alcohol | 9.0 |
| Water for injection | q.s. to 1 ml |

The solutions may be filtered through a 0.2 $\mu$m sterile filter and aseptically filled in ampules. The ampoules are gassed with carbon dioxide.

The present invention accordingly provides a method for the treatment of migraine in a subject in need of such treatment which comprises administering to said subject a therapeutically effective amount of a compound of formula I or II or a pharmaceutically acceptable salt thereof.

We claim:

1. A method of treating migraine in a subject in need of such treatment, which comprises administering to said subject a therapeutically effective amount of E-2-amino-4-methyl-5-phosphono-3-pentenoic acid or a pharmaceutically acceptable salt thereof.

2. A method of treating migraine in a subject in need of such treatment, which comprises administering to said subject a therapeutically effective amount of E-2-amino-4-methyl-5-phosphono-3-pentenoic acid ethyl ester or a pharmaceutically acceptable salt thereof.

3. A method of treating migraine in a subject in need of such treatment, which comprises administering to said subject a therapeutically effective amount of cis-4-phosphonomethyl-2-piperidinecarboxylic acid or a pharmaceutically acceptable salt thereof.

* * * * *